United States Patent [19]

Miles

[11] 4,219,510

[45] Aug. 26, 1980

[54] BENZOXAPHOSPHOLES

[75] Inventor: James A. Miles, Olivette, Mo.

[73] Assignee: Monsanto Company, St. Louis, Mo.

[21] Appl. No.: 55,429

[22] Filed: Jul. 6, 1979

[51] Int. Cl.$^2$ .................... C07F 9/15; A01N 9/36
[52] U.S. Cl. ..................... 260/936; 260/968; 71/86
[58] Field of Search ........................ 260/936

[56] References Cited

U.S. PATENT DOCUMENTS 4,102,949   7/1978   Schliebs, et al. ............ 260/936 X

OTHER PUBLICATIONS

Collins et al., "Aust. J. Chem.", vol. 27, (1974), pp. 1759–1765.
Dennis, et al., "Jou. Am. Chem. Soc.", vol. 88, (1966), p. 3431.
Dannley, et al., "J. Org. Chem.", vol. 26, (1961), p. 3995.
Ludt, et al., "J. Org. Chem.", vol. 36, (1971), p. 1607.
Hellwinkel, et al., "Tetrahedron Letters", vol. 37, (1977) pp. 3241–3244.
Eberhard, et al., "Jou. Am. Chem. Soci.", vol. 87, (1965) p. 253.
Arbuzov, et al., "Chem. Abst.", vol. 76, (1972) 33477h.

Primary Examiner—Anton H. Sutto
Attorney, Agent, or Firm—Steven M. Odre; Donald W. Peterson

[57] ABSTRACT

This disclosure relates to a class of bicyclic hetero compounds. More particularly, this disclosure relates to novel substituted benzoxaphospholes which are useful as herbicides. This disclosure further relates to herbicidal compositions containing such benzoxaphospholes and to herbicidal methods employing such compounds and compositions.

10 Claims, No Drawings

BENZOXAPHOSPHOLES

This invention relates to a class of bicyclic hetero compounds. More particularly, this invention relates to novel substituted benzoxaphospholes which are useful as herbicides. This invention further relates to herbicidal compositions containing such benzoxaphospholes and to herbicidal methods employing such compounds and compositions.

The compounds of the present invention are represented by the formula

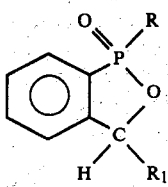

wherein R is selected from the group consisting of hydroxy, lower alkyl, lower alkoxy, phenyl and haloalkylphenyl; and $R_1$ is selected from the group consisting of hydrogen and lower alkyl.

As employed herein, the terms "lower alkyl" and "lower alkoxy" designate alkyl and alkoxy radicals which have up to six carbon atoms in a straight or branched chain. Groups representative of these radicals include, for example, methyl, ethyl, propyl, isopropyl, n-butyl, isobutyl, t-butyl, n-hexyl, methoxy, ethoxy, propoxy, butoxy, n-hexoxy and the like.

The term "halogen" or "halo" as used herein includes chlorine, bromine, fluorine and iodine.

The term "haloalkyl" as employed herein designates alkyl moieties having up to four carbon atoms wherein at least one hydrogen atom has been replaced by a halogen atom. Groups representative of these radicals include, for example, chloromethyl, iodobutyl, dichloroethyl, dibromopropyl, trichloromethyl, trifluoromethyl and the like.

In accordance with the present invention, the novel substituted benzoxaphospholes are prepared by treating a substituted phosphonate of the formula

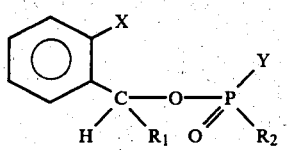

wherein $R_1$ is above defined, $R_2$ is selected from the group consisting of lower alkyl, lower alkoxy, phenyl and haloalkylphenyl, Y is lower alkoxy and X is bromo or iodo; with an organolithium compound in an aprotic solvent.

In conducting the process of this invention, the temperature of the reaction can be from $-80°$ C. to $-65°$ C. It is preferred to conduct the process within a temperature range of $-76°$ C. to $-70°$ C. Temperatures greater than $-65°$ C. give rise to a multitude of by-products and give low yields of the substituted benzoxaphospholes which are difficult to recover.

In preparing the substituted benzoxaphospholes of the present invention, the ratio of reactants is not narrowly critical. For each mole of a phosphonate of formula (II), one should employ at least one mole of an organolithium compound. It is preferred to employ at least 2 moles of an organolithium compound for ease of reaction and recovery of the reaction products.

Illustrative of the organolithium compounds employed in the process of this invention include alkyllithiums such as ethyllithium, butyllithium, t-butyllithium and aryllithiums such as phenyllithium and the like.

Due to the reactive nature of various intermediates and reactants, the process of the present invention should be conducted in an aprotic solvent under anhydrous conditions and in an inert atmosphere. Illustrative of the aprotic solvents employed in the process of this invention include cyclohexane, methylcyclohexane, hexane, benzene, octane, diethyl ether, tetrahydrofuran and the like.

While the process of this invention can be conducted at atmospheric, sub-atmospheric or super-atmospheric pressure, for convenience and economy it is generally preferred to conduct this process at atmospheric pressure.

The phosphonates of formula (II) used as the starting materials in the production of the compounds of this invention are prepared employing the following procedure.

A solution containing a phosphonate ester of the formula

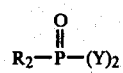

wherein $R_2$ and Y are above defined, in carbon tetrachloride is treated with phosphorus pentachloride at 0° C. under anhydrous conditions. The reaction mixture is stirred for one hour at 0° C., then for 16 hours at 26° C. The resulting solution is concentrated in vacuo and the residue distilled to yield a phosphonic chloride ester of the formula

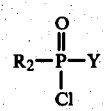

A solution containing the phosphonic chloride ester in anhydrous ether is slowly added over a period of one hour to a mixture of a substituted benzyl alcohol of the formula

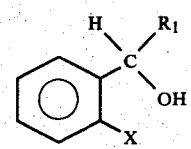

wherein $R_1$ and X are above defined; and 1,5-diazabicyclo[5.4.0]undec-5-ene in anhydrous ether at 0° C. to yield a suspension. The suspension is stirred at 26° C. for one hour, filtered and the ether filtrate is washed with water, then 5% hydrochloric acid, dried over magnesium sulfate and concentrated in vacuo to yield an oil. This oil is distilled under high vacuum to yield the phosphonate of formula (II).

An alternate procedure for preparing the substituted benzoxaphospholes of the present invention involves heating a compound of the formula

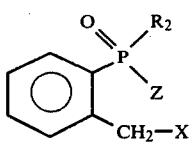

wherein R₂ and X are above defined and Z is hydroxy or alkoxy at a temperature of from 20° C. to 200° C. When employing this alternate procedure, it is possible to increase the rate of reaction and ease of recovery of the reaction products by utilizing an acid catalyst such as perchloric acid.

The P-hydroxyl-benzoxaphospholes of the formula

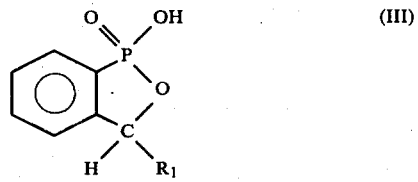

are produced by hydrolyzing a compound of the formula

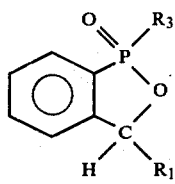

wherein $R_1$ is above defined and $R_3$ is lower alkoxy; at a temperature of from 20° C. to 100° C.

The following illustrative, non-limiting examples will serve to further demonstrate to those skilled in the art the manner in which the specific compounds within the scope of this invention can be prepared. In the examples, all parts are parts by weight unless otherwise expressly stated.

EXAMPLE 1

Under a nitrogen atmosphere a solution of ethyl-2-bromophenyl-3-trifluoromethylphenylphosphonate (2.4 g, 0.00567 mole) in 50 ml. of tetrahydrofuran was cooled to −76° C. in a solid carbon dioxide-acetone bath. To this cooled solution was dropwise added a solution of t-butyllithium (0.74 g, 0.0116 mole) in 6.1 ml. of pentane at a rate such that the temperature of the reaction was maintained below −65° C. The reaction mixture was then stirred for one hour at −76° C. after which time the temperature of the reaction mixture was allowed to rise to 26° C. over a period of 45 minutes. The reaction was quenched with the addition of 1 ml. of acetic acid. The reaction mixture was concentrated to yield a yellow residue which was partitioned between methylene chloride and water. The methylene chloride layer was dried over magnesium sulfate and concentrated in vacuo to yield a yellow glass-like residue. The glass-like residue was distilled to yield a colorless oil which was crystallized upon trituration in petroleum ether to yield 1-[3-(trifluoromethyl)phenyl]-1,3-dihydro-2,1-benzoxaphosphole-1-oxide (0.85 g, 51% yield) as a white solid having a melting point of 102°–106° C. and the following analysis:

Calculated: C, 56.39; H, 3.38. Found: C, 56.41; H, 3.46.

EXAMPLE 2

A mixture of 2-bromomethylphenyl-phenylphosphonic acid (3.95 g, 0.0127 mole) and 10 ml. of 10% perchloric acid was heated at 100° C. for 4.5 hours with constant stirring. The reaction mixture was cooled to 26° C. and then extracted with methylene chloride. The methylene chloride layers were washed with brine, dried over sodium sulfate and concentrated in vacuo to yield a yellow oil. This oil was distilled in a Kugelrohr at 180° C. and 0.6 torr to yield a colorless oil. The colorless oil was slurried in anhydrous diethyl ether, cooled during which period crystallization occured and then filtered to yield 1-phenyl-1,3-dihydro-2,1-benzoxaphosphole-1-oxide (2.2 g, 76% yield) as white crystals having a melting point of 99°–101° C. and the following analysis:

Calculated: C, 67.83; H, 4.82. Found: C, 67.63; H, 4.80.

EXAMPLE 3

A mixture of 2-bromomethylphenyl-methyl-phosphonic acid (12.25 g, 0.05 mole) and 50 ml. of 10% perchloric acid was heated at 100° C. for 0.5 hours with constant stirring. The reaction mixture was cooled to 26° C., then extracted with methylene chloride. The methylene chloride layers were dried over anhydrous potassium carbonate, filtered through celite and concentrated in vacuo to yield a tan oil. This oil was distilled in a Kugelrohr at 150° C. and 0.1 torr to yield a colorless oil. The colorless oil was slurried in anhydrous diethyl ether, cooled and then filtered to yield a solid. Recrystallization of the solid from diethyl ether yielded 1-methyl-1,3-dihydro-2,1-benzoxaphosphole-1-oxide (5.5 g, 66% yield) as a colorless solid having a melting point of 70°–72° C. and the following analysis:

Calculated: C, 57.14; H, 5.36. Found: C, 57.02; H, 5.39.

EXAMPLE 4

A mixture of diethyl-2-bromoethylphenylphosphonate (2.2 g, 0.00717 mol) in 25 ml. of 1,2-dichlorobenzene was refluxed for 10 hours. The resulting mixture was vacuum distilled. Fractions containing the benzoxaphosphole were collected and then taken up in a hot mixture of benzene-petroleum ether. The mixture was cooled while adding sufficient benzene to prevent oiling out. The cooled mixture yielded 1-ethoxy-1,3-dihydro-2,1-benzoxaphosphole-1-oxide (1.06 g, 75% yield) as colorless crystals having a melting point of 60° C. and the following analysis:

Calculated: C, 54.61; H, 5.55. Found: C, 54.80; H, 5.61.

EXAMPLE 5

A mixture of 1-ethoxy-1,3-dihydro-2,1-benzoxaphosphole-1-oxide (4.0 g, 0.02 mole) in 15 ml. of water was heated on a steam bath for 1 hour. The reaction mixture was taken to dryness under vacuum and the residue recrystallized from acetone to yield 1-hydroxy-1,3-dihydro-2,1-benzoxaphosphole-1-oxide (3.4 g, 100% yield) as colorles crystals having a m.p. of 167° C. and the following analysis:

Calculated: C, 49.40; H, 4.12. Found: C, 49.26; H, 4.10.

EXAMPLE 6

A mixture of diethyl-2-(1-bromoethyl)phenylphosphonate (12 g, 0.037 mole) in 25 ml. of 1,2-dichlorobenzene was refluxed for 2 hours. The reaction mixture was vacuum distilled to yield 1-ethoxy-3-methyl-1,3-dihydro-2,1-benzoxaphosphole-1-oxide (4.3 g, 55% yield) as a colorless oil.

The 1-ethoxy-3-methyl-1,3-dihydro-2,1-benzoxaphosphole-1-oxide was added to 25 ml. of water and then heated on a steam bath for 1 hour. The reaction mixture was cooled, washed with chloroform and taken to dryness under vacuum to yield a clear oil which crystallized upon scratching. Recrystallization from acetone-ether yielded 1-hydroxy-3-methyl-1,3-dihydro-2,1-benzoxaphosphole-1-oxide as a white powder. A second crop was obtained from the filtrate to give a total yield of 2.4 g (67% yield) of 1-hydroxy-3-methyl-1,3-dihydro-2,1-benzoxaphosphole-1-oxide having a melting point of 148°–149° C. and the following analysis:

Calculated: C, 52.20; H, 4.89. Found: C, 52.24; H, 4.77.

EXAMPLE 7

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the table. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the table under WAT and the results recorded. In some instances, the two-week observations are omitted.

The post-emergence herbicidal activity index used in Table I is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A - Canada Thistle* | G - Yellow Nutsedge* |
| B - Cocklebur | H - Quackgrass* |
| C - Velvetleaf | I - Johnsongrass* |
| D - Morningglory | J - Downy Brome |
| E - Lambsquarters | K - Barnyardgrass |
| F - Smartweed | |

*Established from vegetative propagules.

Table I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 2 | 56.0 | 0 | 0 | 0 | 0 | 1 | 2 | 0 | 0 | 0 | 0 | 2 |
| 1 | 2 | 11.2 | 0 | 0 | 0 | 0 | 0 | 0 | 0 | 0 | 0 | 0 | 0 |
| 2 | 2 | 11.2 | 0 | 0 | 1 | 0 | 4 | 0 | 0 | 0 | 0 | 0 | 0 |
| 3 | 2 | 56.0 | 1 | 1 | 0 | 0 | 0 | 1 | 0 | 0 | 0 | 0 | 1 |
| 3 | 2 | 11.2 | 0 | 0 | 0 | 0 | 0 | 0 | 0 | 0 | 0 | 0 | 0 |
| 4 | 2 | 11.2 | 0 | — | 0 | 1 | 1 | 0 | 0 | 0 | 0 | 0 | 0 |
| 5 | 2 | 11.2 | 0 | 1 | 0 | 1 | 2 | 0 | 0 | 0 | 0 | 0 | 0 |
| 6 | 2 | 56.0 | 0 | 0 | 0 | 0 | 0 | 0 | 0 | 0 | 0 | 0 | 2 |
| 6 | 2 | 11.2 | 0 | 0 | 0 | 0 | 0 | 0 | 0 | 0 | 0 | 0 | 0 |

It was also noted that 1-hydroxyl-3-methyl-1,3-dihydro-2,1-benzoxaphosphole-1-oxide exhibited pre-emergent herbicidal activity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific benzoxaphosphole employed. In foliar treatment for the control of vegetative growth, the active ingredients are applied in amounts from about 0.112 to about 56.0 or more kilograms per hectare. In pre-emergent treatments, the rate of application can be from about 2.24 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

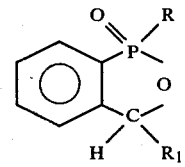

wherein R is selected from the group consisting of hydroxy, lower alkyl, lower alkoxy, phenyl and haloalkyl phenyl; and $R_1$ is selected from the group consisting of hydrogen and lower alkyl.

2. A compound according to claim 1 wherein $R_1$ is hydrogen.

3. A compound according to claim 2 wherein the compound is 1-phenyl-1,3-dihydro-2,1-benzoxaphosphole-1-oxide.

4. A compound according to claim 2 wherein the compound is 1-[3-(trifluoromethyl)phenyl]-1,3-dihydro-2,1-benzoxaphosphole-1-oxide.

5. A compound according to claim 2 wherein the compound is 1-methyl-1,3-dihydro-2,1-benzoxaphosphole-1-oxide.

6. A compound according to claim 2 wherein the compound is 1-ethoxy-1,3-dihydro-2,1-benzoxaphosphole-1-oxide.

7. A compound according to claim 2 wherein the compound is 1-hydroxy-1,3-dihydro-2,1-benzoxaphosphole-1-oxide.

8. A compound according to claim 1 wherein $R_1$ is lower alkyl.

9. A compound according to claim 8 wherein the compound is 1-ethoxy-3-methyl-1,3-dihydro-2,1-benzoxaphosphole-1-oxide.

10. A compound according to claim 8 wherein the compound is 1-hydroxy-3-methyl-1,3-dihydro-2,1-benzoxaphosphole-1-oxide.

* * * * *